United States Patent [19]

Weickgenannt

[11] Patent Number: 4,936,836

[45] Date of Patent: Jun. 26, 1990

[54] DRAIN BAG SUPPORT ASSEMBLY

[75] Inventor: Egon R. Weickgenannt, Cincinnati, Ohio

[73] Assignee: Liebel-Flarsheim Company, Cincinnati, Ohio

[21] Appl. No.: 257,342

[22] Filed: Oct. 13, 1988

[51] Int. Cl.$^5$ .................. A61M 1/00; A61B 19/00
[52] U.S. Cl. .................................. 604/322; 604/356; 128/31; 108/24; 108/26
[58] Field of Search .................. 248/99–101, 248/118; 604/322, 356, 357, 317; 108/24–26; 232/1 B, 1 E; 269/327, 328; 128/361, 31, 845, 849, 851

[56] References Cited

U.S. PATENT DOCUMENTS

| | | |
|---|---|---|
| 1,653,393 | 12/1927 | Cox . |
| 2,149,042 | 2/1939 | Branthover . |
| 3,260,488 | 7/1966 | Kliewer et al. . |
| 3,386,444 | 6/1968 | Brenner et al. . |
| 4,007,741 | 2/1977 | Waldrop et al. ........... 604/357 |
| 4,179,159 | 12/1979 | Sieklucki et al. . |
| 4,221,371 | 9/1980 | Kuphal . |
| 4,287,422 | 9/1981 | Kuphal et al. . |

OTHER PUBLICATIONS

Siemans brochure "UROSKOP B2: Urological X-Ray examination table", pp. 2-10.

Primary Examiner—Richard J. Apley
Assistant Examiner—Jennifer Doyle
Attorney, Agent, or Firm—Wood, Herron & Evans

[57] ABSTRACT

A drain bag support assembly has a multi-sided frame with pivotally interconnected parts that are vertically rigid, yet movable in a horizontal direction to varyingly distort the configuration of the frame. One part of the frame is removably connectable to an examining end of a urological table while a second part, opposite the first, has a pair of elbow pads mounted at opposite ends thereof to provide elbow support for a urologist seated adjacent the examining end of the table. The first and second parts of the frame support an upwardly opening drain bag, and the first and second parts are pivotally interconnected by a pair of spaced side arms. Each side arm has a first side member and a second side member pivotally connected to an intermediate plate. With elbows vertically supported by the pads, the urologist can change the configuration of the frame with respect to the table simply by moving the elbows in a horizontal direction. The shape of the bag conforms to the new configuration of the frame while at all times providing drainage and remaining between the urologist and the examining end of the table.

20 Claims, 4 Drawing Sheets

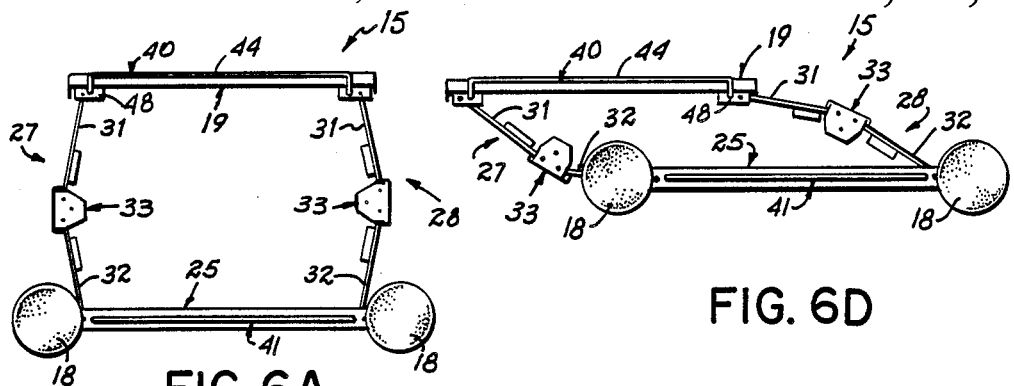
FIG. 6A
FIG. 6D
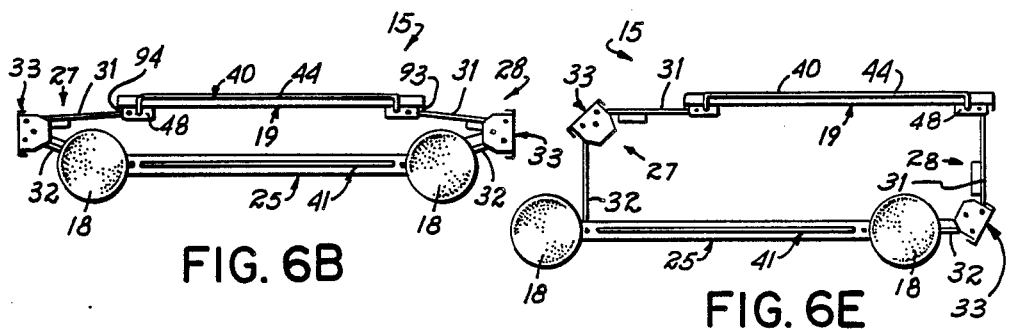
FIG. 6B
FIG. 6E
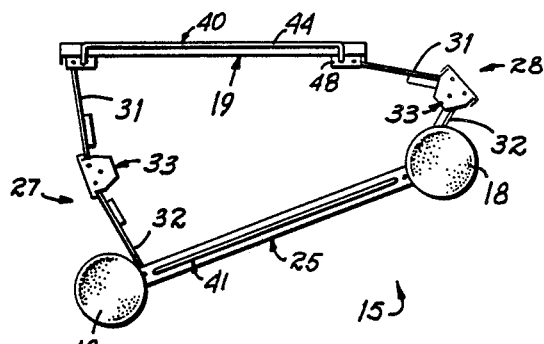
FIG. 6C

DRAIN BAG SUPPORT ASSEMBLY

FIELD OF THE INVENTION

This invention relates to a drain bag support assembly that is connectable to an examining end of a urological table.

BACKGROUND OF THE INVENTION

Brenner, et al. U.S. Pat. No. 3,386,444, expressly incorporated herein by reference in its entirety, discloses a urological drain bag assembly mounted to one end of a urological table. Such devices enable fluid collection to take place while a urologist performs an examination and/or a medical procedure. Typically, due to the desirability of minimizing interference with the urologist, these devices locate the bag between a patient supported on the table and a urologist sitting near the end of the table.

The cited Brenner patent discloses a drain bag and hinged support means which can be pivoted down and up between a fully open position, through an attitude affording maximum splash protection, to a fully closed position in which the bag and support are completely out of the way and permit maximum "elbow room" to the urologist. FIG. 2 shows the open position, with the device mounted to the table for pivotal movement about a horizontal axis, thereby enabling a splash protector to rotate about the axis to provide better splash protection as the urologist moves toward or away from the table. FIGS. 7-10 show a modified form of the drain bag support.

A publication by Siemens entitled "Uroskop B 2: Urological X-Ray Examination Table" discloses a pair of spaced elbow supports pivotally mounted on opposite sides of a urological table at an examining end thereof. While such elbow supports may provide some degree of convenient and steady support for the elbows of a urologist when sitting relatively close to the end of the table, no support is provided beyond this distance. If required to move away from the table beyond this distance, the urologist will eventually have to perform without steady elbow support. Moreover, table mounted supports of this type, although pivotal, do not provide sufficient freedom of movement. If additional freedom of movement is necessary, the urologist must contort his or her body position in order to keep the elbows on the supports.

Plum, U.S. Pat. No. 3,653,619 discloses a garbage bag holder of mutually articulated rod elements, one of the rod elements being connected to a cupboard door and another of the rod elements being connected to a frame to which the door is hinged. The bag holder is transferred from a closed position to an open position when the door is opened from the frame, and from an open position to a closed position when the door is closed.

It is an object of this invention to provide an improved drain bag support assembly which permits increased maneuverability of the urologist with respect to the table, while at the same time provides the urologist maximum convenience and steady support during the performance of a medical procedure.

SUMMARY OF THE INVENTION

To these ends, this inventive drain bag assembly has a multi-sided, collapsible frame of pivotally interconnected segments which are rigid in a vertical direction and movable in a horizontal direction to varyingly distort the configuration of the frame. Preferably, a first of the segments is removably connectable to an examining end of a urological table and a second of the segments, opposite the first, has elbow pads mounted at opposite ends thereof. The opposing first and second segments support opposite sides of a urological drain bag that is located within the frame. Preferably, the bag is mounted to raised front and rear rails which extend upwardly from the front and rear frame segments, respectively.

The pads provide steady vertical elbow support for a urologist during the performance of a medical procedure, while the frame enables this support to be provided in such a manner that the urologist is permitted a maximum freedom of horizontal movement relative to the table, while the bag at all times provides its drain function regardless of the pad position, and hence frame shape. During movement, the configuration of the frame changes, depending upon the exact location of the elbows. The configuration of the supported drain bag will change accordingly, thus tracking the movement of the elbows of the urologist without interfering with his or her movement relative to the end of the table.

Preferably, the frame has a first or front segment for mounting to the examining end of the table, a rear segment to which the pair of elbow pads is mounted at opposite ends thereof, and pivotally interconnected side arms connecting the opposite ends of the front and rear segments. Each side arm includes a front side member pivotally connected to one end of the front segment, and a rear side member pivotally connected to one end of the rear segment. At their other ends, the front and rear side members are both pivotally connected to an intermediate plate. Front and rear ears are mounted to the front side member and the rear side member, respectively, and the ears are further connected to the intermediate plate by helical springs which bias the connected side members outwardly from the plate.

When connected to the table, the pivotal interconnections between the segments, the side members and the plates enable the frame to be moved in a horizontal plane relative to the table, providing a wide variety of frame configurations, while the frame remains vertically rigid. This multi-sided collapsible frame of pivotally interconnected parts, the parts including the two front and rear segments, the four front and rear side members and the two plates, has a total of eight vertical axes of pivotal movement. As the urologist maneuvers with respect to the table, the frame provides rigid elbow support in a variety of convenient locations, each location corresponding to a particular frame configuration.

These and other objects and features of the invention will be more readily appreciated in view of the following detailed description and the drawings in which:

BRIEF DESCRIPTION OF THE DRAWINGS

FIGS. 6a—6e show plan views of the frame oriented in five different configurations.

DETAILED DESCRIPTION OF THE DRAWINGS

Figure 1:
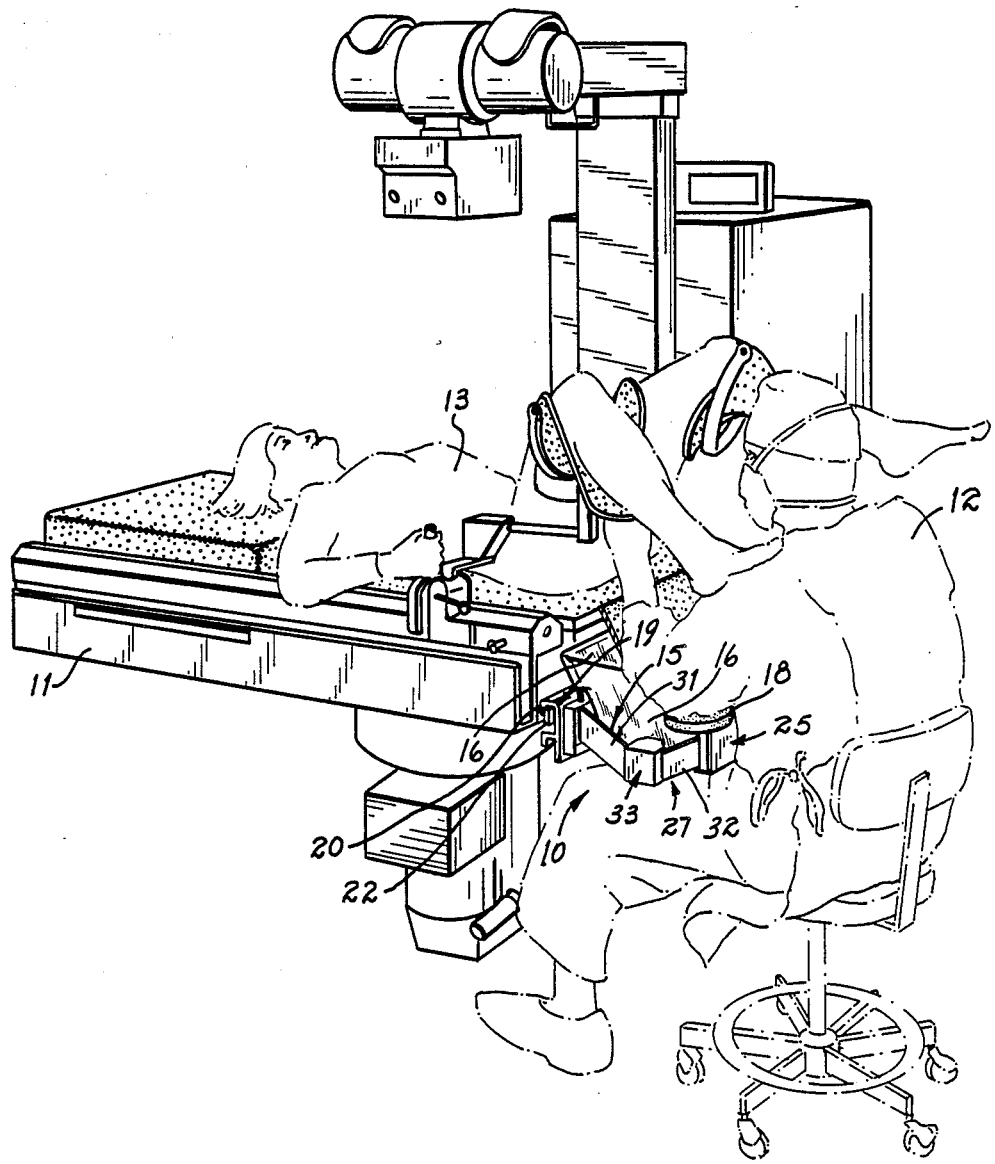
FIG. 1 is a perspective view of a urological table equipped with a drain bag support assembly in accordance with a preferred embodiment of the invention.

FIG. 1 shows a drain bag assembly 10 in accordance with a preferred embodiment of the invention, the assembly 10 connected to an examining end of a urological table 11. This drain bag assembly 10 provides increased versatility and steadiness for a urologist 12 in performing a medical examination or procedure upon a patient 13 supported on the table 11. More specifically, the drain bag assembly 10 has a multi sided, collapsible frame 15 which supports a disposable drain bag 16 between the urologist 12 and the table 11, the frame 15 providing elbow pads 18 to support the elbows of the urologist 12. The bag 16 performs a drain function. That is, it collects excess body fluid at the end of the table 11 for drainage therethrough or disposal in another manner. The frame 15 maintains vertical rigidity, but is maneuverable in a horizontal plane by the elbows of the urologist 12 into a variety of possible configurations, thus maximizing the number of positions in which both steady elbow support and fluid collection can be provided. Moreover, because the frame 15 moves with the elbows, and the bag 16 conforms to the configuration of the frame 15, the assembly 10 does not interfere with movement of the urologist 12 relative to the table 11.

A first, or front frame segment 19 of the bag assembly 10 includes a three sided channel 20 which slidably mounts the assembly 10 onto a retaining plate 22 rigidly supported by the table 11. The channel 20 is preferably bolted to the front segment 19, but may be fixedly secured in any other suitable manner. The front segment 19 is preferably about 17" long. The elbow pads 18 are mounted to a second, or rear frame segment 25, which is opposite to front segment 19 and is preferably about 21" long. The pads 18 may be hard plastic and formed by molding, or cushioning material sandwiched by vinyl.

Figure 2:
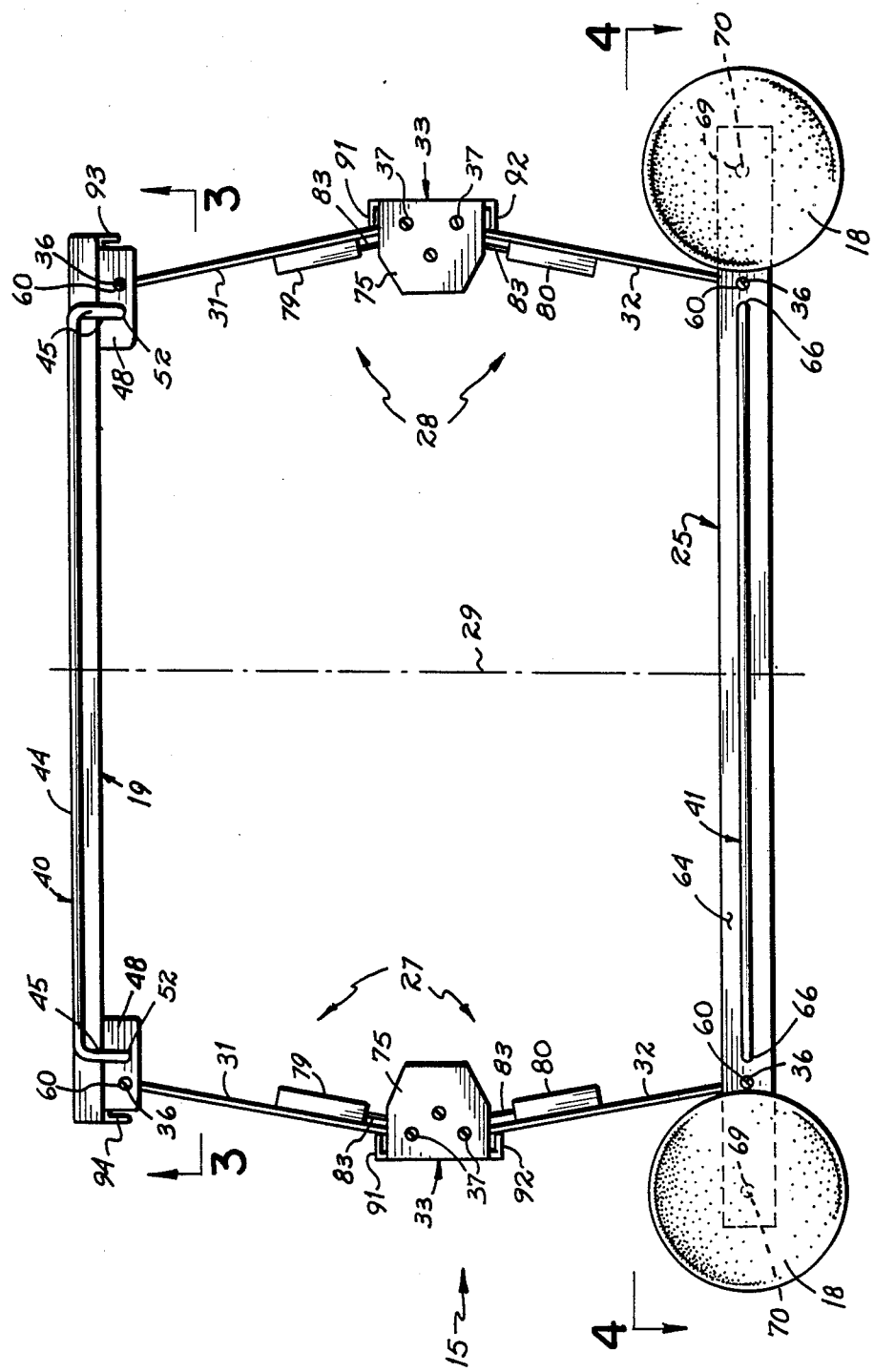
FIG. 2 is a plan view of the frame of a drain bag support assembly in accordance with a preferred embodiment of the invention.

As shown in FIG. 2, the front and rear frame segments 19 and 25 are interconnected on opposite sides at ends thereof by spaced side arms 27 and 28, which are mirror images of each other with respect to a central axis 29 extending longitudinally of the table 11 (not shown) and assembly 10. Each of the side arms has a first or front side member 31 hingedly connected along a vertical axis to an end of front frame segment 19 and a second or rear side member 32 hingedly connected along a vertical axis to an end of rear frame segment 25. Each of the side members 31 and 32 is preferably about 5¼" long. On each side of the frame 15, between segments 19 and 25, the front side member 31 and the rear side member 32 are pivotally interconnected along vertical axes to an intermediate plate 33.

The frame 15 provides pivotal movement about eight separate vertical axes of interconnection, four of the axes located where each of the side members 31 and 32 are connected to the frame segments 19 and 25, each designated as 36, and four of the axes located where the side members 31 and 32 are connected to the intermediate plates 33, each designated as 37. Thus, the interconnected frame 15 is horizontally movable into a wide variety of configuration, while at all times remaining vertically rigid. While being pivotally connected at both ends for horizontal movement, each of the interconnected parts of the frame 15 must have sufficient structural rigidity so as not to distort vertically when weight is applied to the pads 18. Preferably, the parts are formed from sheet metal, and are pivotally interconnected along vertical edges.

The pads 18 enable the urologist 12 to steadily support the elbows on the assembly 10 during a procedure. The pivotal interconnections at axes 36 and 37 permit maximum maneuverability in the horizontal plane occupied by the frame 15, with movement permitted toward or away from the table 11 or from side to side with respect to axis 29. Preferably, at the opposite ends of rear frame segment 25, the elbow pads 18 are mounted outboard of the rear axes of interconnection 36, as shown clearly in FIG. 2.

Opposite sides of the mouth of the drain bag 16 are supported at front frame segment 19 and rear frame segment 25 by front rail 40 and rear rail 41, respectively. Because the configuration of the mouth of the bag 16 changes according to the configuration of the frame 15, the bag 16 must be of sufficient size to extend longitudinally from front rail 40 to rear rail 41 when the distance between the front and rear segments is at a maximum, as shown in FIG. 2. Preferably, rails 40 and 41 and the bag 16 also extend substantially across the maximum width of the frame 15, this maximum width corresponding to the distance between the intermediate plates 37 when the frame 15 is configured as in FIG. 2.

Front rail 40 preferably has a horizontally disposed intermediate portion 44 located between generally vertically disposed end portions 45. As shown in FIG. 2, the vertically disposed end portions 45 of rail 40 do not extend straight up for their entirety, but are preferably offset horizontally somewhat to extend in the direction of the table 11 when front segment 19 is mounted thereto. This locates the mouth of the bag 16 closer to the patient 13.

Figure 3:
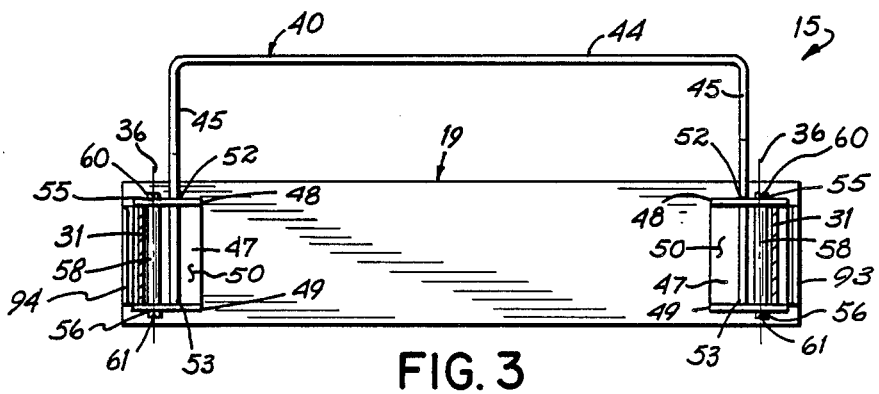
FIG. 3 is a cross-sectional view taken along lines 3—3 of FIG. 2.

The ends 45 of the rail 40 are mounted to the frame segment 19 by opposite, endwise-mounted channels 47, shown in FIG. 3. Each of the channels 47 has a top horizontal portion 48 and a bottom horizontal portion 49 connected to a middle portion 50 that is fixedly secured to frame segment 19. Preferably, each end 45 extends vertically through an aperture 52 in top portion 48, and has a bottom tip 53 that is secured to bottom portion 49 by welding.

To mount the front side member 31 to the frame segment 19, according to a preferred embodiment of the invention, each of the channels 47 has aligned top 55 and bottom 56 holes machined therethrough along the respective vertical axis 36 of connection. A vertically directed eye (not shown) along a forward edge 58 of each front side member 31 is aligned with holes 55 and 56. An elongated stand-off (not shown) having female threads at both ends is aligned along axis 36 within the eye and secured in place by a top screw 60 above top portion 48 and a bottom screw 61 beneath bottom portion 49.

Figure 4:
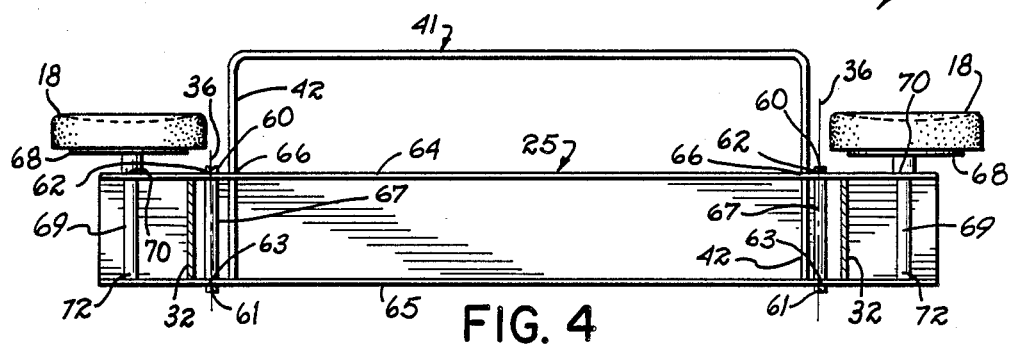
FIG. 4 is a cross-sectional view taken along lines 4—4 of FIG. 2.

As shown in FIG. 4, rear rail 41 and the rear side members 32 are connected to rear frame segment 25 in a similar fashion. A top horizontally directed surface 64 and a bottom horizontally directed surface 65 are preferably formed as integral portions of frame segment 25. At each end of segment 25, a vertically directed portion 42 of rear rail 41 extends through a hole 66 in surface 64 and is welded to surface 65. Alternately, in connecting either of rails 40 or 41 to the respective frame segments, hollow bottom tips of the rails can be female threaded, aligned with holes in the bottoms of the respective segments, and secured by screws. A vertically directed eye (not shown) along a back edge 67 of each rear side member 32 is aligned along holes 62 and 63 in surfaces 64 and 65, respectively, and connection is made in the same manner as described above with respect to the front side members 31 and front frame segment 19. A stand-off with female threads is aligned along axis 36 and secured by a top screw 60 and a bottom screw 61.

Because each of the side members is secured to the frame segments along a vertical edge by a vertically directed eye aligned along a vertical axis of rotation, horizontal movement of the frame 15 is allowed while vertical rigidity of the frame 15 and each of the individual parts is maintained. Alternate forms of connection between the side members 31 and 32 and the frame segments 19 and 25 and plates 33 may be utilized, so long as these connections provide horizontal hinging and vertical rigidity of the frame 15.

FIG. 4 also shows the details of connection for the elbow pads 18 mounted at opposite ends of the frame segment 25. Each pad 18 is preferably secured to a circular plate 68 that is welded to the top of an elongated stem 69. Each of the stems 69 extends downwardly through an aperture 70 in top surface 64 and further downwardly to be supported by bottom surface 65. Bottom tips 72 of the stems 69 may be secured to the bottom surface 65. However, for increased maneuvering versatility, it is preferable to leave the tips 72 unsecured to bottom surface 65, thereby allowing the stems 69 to rotate with respect to the frame segment 25. This enables the elbow pads 18 to rotate with respect to segment 25 as the frame 15 is maneuvered. Alternately, to provide for pad rotation with respect to frame segment 25, a bushing assembly may be provided between top surface 64 and bottom surface 65 to receive a stem 69 connected to the pad 18.

Figure 5:
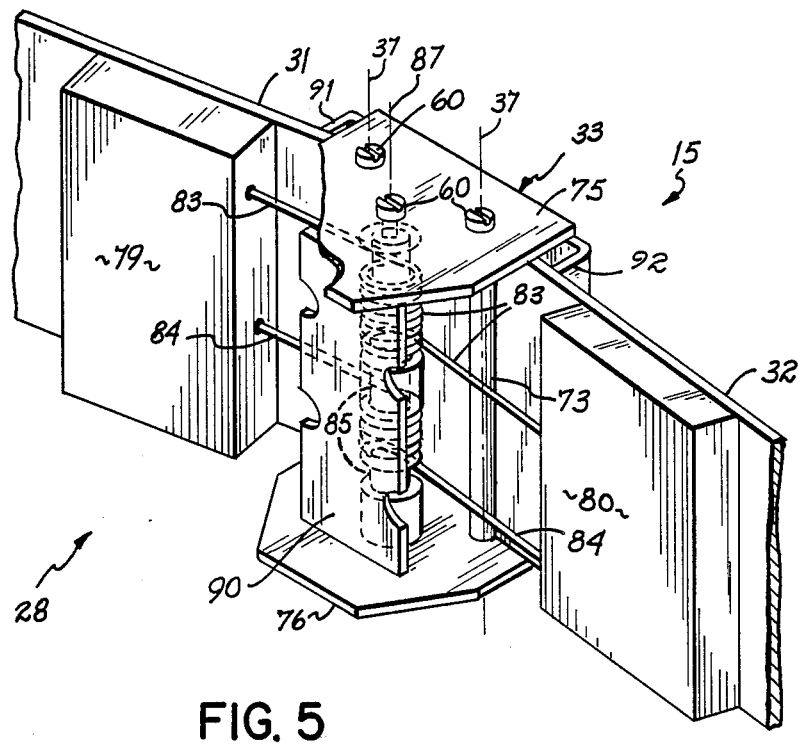
FIG. 5 is a perspective view of an intermediate plate assembly pivotally connected to first and second side members in accordance with a preferred embodiment of the invention.

FIG. 5 shows the connections among a front side member 31, an intermediate plate 33 and a rear side member 32 on one side of the frame 15. At each axis 37, pivotal connection is made in the same manner as described with respect to the side member connections to the frame segments. A vertically directed eye (not shown) formed along the edge 73 of the respective side member is aligned with a pair of holes in a top portion 75 and a bottom portion 76 of the plate 33. An elongated stand-off (not shown) aligned along axis 37 is extended through the aligned holes and eye and secured above top portion 75 by a top screw 60 and below bottom portion 76 by a bottom screw 61 (not shown). Again, in securing the side members 31 and 32 to the plate 33 for pivotal movement with respect thereto, vertical integrity of the frame 15 is maintained by aligning and securing an edge-located, vertically directed eye along a vertical axis of rotation. If desired, spacers may be provided between the top and bottom ends of the eyes and the respective top and bottom portion of the plates and segments.

Front side member 31 and rear side member 32 are further connected to plate 33 by a front depending ear 79 and a rear depending ear 80, respectively, and a spring assembly. The ears 79 and 80 are bolted to the respective side members 31 and 32. A top helical wire spring 83 and a bottom helical wire spring 84 urge the connected side members outwardly. Portions of the helical wire springs 83 and 84 are concentric with a metal sleeve 85 that extends along a spring axis 87. The sleeve 85 has female threads at both ends, and is held in place at the top portion 75 of the plate 33 by an upper screw 60 and at the bottom portion 76 of the plate 33 by a lower 61 screw. Metal sleeve 85 and the springs 83 and 84 are partially hidden from view by an inboard plate 90 which also extends between the top 75 and bottom 76 portions of plate 33. The springs 83 and 84 urge the side members 31 and 32 outwardly to a position where they are abutted by side flanges 91 and 92, respectively, thereby limiting the angle between the side members to a maximum of about 160°.

FIGS. 6a–6e show five of the various configurations that are made possible by the multi-sided frame 15 of this assembly 10. FIG. 6a shows a plan view of the frame 16 at its outwardly urged position, as shown in FIG. 2. This position provides elbow support at the maximum distance from the table 11 and the distance from rail 40 to rail 41 is about 12".

FIG. 6b shows the frame 15 collapsed in the direction of the table 11, with side arm 27 and side arm 28 hinged inwardly to about the maximum inward position. This configuration provides elbow, support at about the minimum distance from the table 11. In this position, side flanges 93 and 94 located at opposite ends of frame segment 19 abuttingly engage the front side members 31 to prevent further pivotal movement of the side members 31 with respect to the frame segment 19. At the maximum inward, or closed, position, the distance from rail 40 to rail 41 is about 2 ¼".

FIG. 6c shows the frame 15 in a configuration whereby side arm 27 is biased outwardly at about the maximum angle, and side arm 28 is bent inwardly somewhat from this maximum outward position. FIG. 6d shows the frame 16 configured to a position which provides elbow support at about the maximum side distance with respect to the table, side arms 27 and 28 both angled outwardly at approximately 160°. FIG. 6e shows another of the variety of possible frame configurations for the drain bag support assembly 10 of this invention.

For each of these configurations, the mouth of the drain bag 16 must conform to the shape bordered by front segment 19, rear segment 25 and side arms 27 and 28 in order to provide fluid collection, or drainage, at the end of the table 11, regardless of the configuration of the frame 15. The mouth of the drain bag 16 must be sufficiently secured to the front and rear rails 40 and 41, respectively. Securement to the rails can be accomplished by providing front and rear pockets to fit over the rails, or by simply pinning the bag in open position at the rails.

A preferred embodiment of the drain bag support assembly in accordance with this invention has been described, it is to be understood that the invention is not limited thereby and then in light of the present disclosure, various other alternative embodiments will be apparent to one of ordinary skill in the art. Accordingly, it is to be understood that various changes may be made without departing from the scope of the invention is particularly set forth in claims.

I claim:
1. A drain bag assembly comprising:
  a multi-sided collapsible frame of pivotally interconnected parts, a first of said parts being removably connectable to one end of a urological table, said frame being rigid in a vertical direction and movable in a horizontal direction to varyingly distort the configuration of the frame;

elbow support means mounted to a second of said pivotally connected parts, said second part being opposite to said first part;

a drain bag supported by said frame to provide a drain function at said one end of said table; and said elbow support means providing elbow support for a urologist performing a medical procedure on a patient on said table, whereby movement of said supported elbows changes the configuration of the frame while supporting the bag without said bag or said frame substantially interfering with movement of the urologist relative to the table and further without interfering with the drain function of the bag.

2. The drain bag assembly of claim 1 wherein said pivotally interconnected parts are interconnected about eight axes of pivotal movement.

3. The drain bag assembly of claim 1 and further comprising:

a raised rail extending upwardly from said first part;

a raised rail extending upwardly from said second part, said raised rails supporting opposite sides of said drain bag.

4. The drain bag assembly of claim 3 wherein said raised rail extending upwardly from said first part is offset in a horizontal direction toward said one end of the urological table when said first part is connected thereto.

5. The drain bag assembly of claim 1 wherein said first and second parts are interconnected on opposite sides thereof by side arms, each said side arm further comprising:

a first side member having a first edge pivotally connected to said first part at an end thereof;

a second side member having a second edge pivotally connected to said second part at an end thereof; and an intermediate plate pivotally interconnected to said first and second side members between said first and second parts.

6. The drain bag assembly of claim 5 wherein each said pivotally interconnected side member is further connected to said intermediate plate by an ear spring assembly, said ear spring assembly biasing said first and second side members outwardly from said intermediate plate.

7. The drain bag assembly of claim 6 wherein said intermediate plate further comprises first and second side flanges to limit said outward biasing of said first and second side members to a maximum angle of about 160°.

8. The drain bag assembly of claim 1 wherein said first part further comprises a channel adapted to slidably connect said frame to said one end of said table.

9. The drain bag assembly of claim 1 wherein said elbow support means includes pads located at opposite ends of said second part which are mounted for rotational movement with respect to said second part.

10. A drain bag support assembly comprising:

a first frame segment releasably connectable to an end of a urological table, said first frame segment adapted to support a first end of a drain bag;

a second frame segment adapted to support a second end of said drain bag opposite said first end and interconnected to said first frame segment by a pair of spaced side arms, said drain bag providing a drain function at said end of the table;

said frame segments and said side arms being pivotally interconnected to provide a frame for surrounding said supported drain bag, said frame being rigid in a vertical direction and movable in a horizontal direction to varyingly distort the configuration of the frame, thereby rendering said second frame segment horizontally movable relative to said table when said first segment is connected thereto; and a pair of elbow pads mounted to opposite ends of said second frame segment, said elbow pads providing rigid vertical support for a urologist's elbows at variable frame positions selectable by movement of the elbows in said horizontal plane while also permitting the bag to track movement of the elbows and frame without interfering with relative movement of the urologist with respect to the table, and further without interfering with the drain function of the bag.

11. The drain bag assembly of claim 10 wherein each said side arm further comprises:

a first side member pivotally connected to said first frame segment;

a second side member pivotally connected to said second frame segment;

an intermediate plate pivotally interconnected to said first and second side members between said first and second frame segments;

a spring assembly located at said intermediate plate for outwardly biasing said pivotally interconnected first and second side members.

12. The drain bag assembly of claim 10 wherein said elbow pads are mounted for rotation with respect to said second frame segment.

13. The drain bag assembly of 10 wherein said elbow pads mounted at said opposite ends of said second frame segment are located outside of said interconnected side arms.

14. The drain bag assembly of claim 1 wherein said drain bag is supported by said first and second parts and located within said frame.

15. A drain bag support assembly comprising:

a multi-sided collapsible frame, including:

(a) a first frame segment releasably connected to an end of a urological table;

(b) a second frame segment interconnected to said first frame segment by a pair of spaced side arms, said frame segments and said side arms being pivotally interconnected to provide said frame;

(c) said frame supporting a drain bag to provide a drain function at said end of the table;

(d) said frame being rigid in a vertical direction and movable in a horizontal direction to varyingly distort the configuration of the frame, thereby rendering said second frame segment horizontally movable relative to said table when said first segment is connected thereto; and (e) support means mounted to said second frame segment for providing rigid vertical support for a urologist's elbows at variable frame positions selectable by movement of the elbows in said horizontal plane while also permitting the bag to track movement of the elbows and frame without interfering with relative movement of the urologist with respect to the table, and further without interfering with the drain function of the bag.

16. The drain bag support assembly of claim 15 wherein each said side arm further comprises:
 - a first side member pivotally connected to said first frame segment;
 - a second side member pivotally connected to said second frame segment;
 - an intermediate plate pivotally interconnected to said first and second side members between said first and second frame segments;
 - a spring assembly located at said intermediate plate for outwardly biasing said pivotally interconnected first and second side members.

17. The drain bag support assembly of claim 15 wherein said support means includes elbow pads mounted at opposite ends of said second frame segment.

18. The drain bag support assembly of claim 17 wherein said elbow pads are rotatably mounted to said second frame segment and located outside of said interconnected side arms.

19. The drain bag support assembly of claim 18 wherein said drain bag is supported by said first and second frame segments and located within said frame.

20. An apparatus comprising, in combination:
 - a urological table having a head end and a foot end;
 - a multi-sided collapsible frame of pivotally interconnected parts, a first of said parts being removably connectable to said foot end of said urological table, said frame being rigid in a vertical direction and movable in a horizontal direction to varyingly distort the configuration of the frame;
 - elbow support means mounted to a second of said pivotally connected parts, said second part being opposite to said first part;
 - a drain bag supported by said frame to provide a drain function at said foot end of said table; and
 - said elbow support means providing elbow support for a urologist performing a medical procedure on a patient on said table, whereby movement of said supported elbows changes the configuration of the frame while supporting the bag without said bag or said frame substantially interfering with movement of the urologist relative to said table and further without interfering with the drain function of the bag.

* * * * *